United States Patent [19]

Schlüter

[11] Patent Number: 5,160,704
[45] Date of Patent: Nov. 3, 1992

[54] METHOD AND APPARATUS FOR COLLECTING AND SEPARATING PARTICLES FROM FLUID FOR MEDICAL DIAGNOSIS

[75] Inventor: Gert Schlüter, Gundelfingen, Fed. Rep. of Germany

[73] Assignee: Remedia AG, Basel, Switzerland

[21] Appl. No.: 827,573

[22] Filed: Jan. 29, 1992

Related U.S. Application Data

[63] Continuation of Ser. No. 458,153, Dec. 28, 1989, abandoned.

[30] Foreign Application Priority Data

Feb. 17, 1989 [DE] Fed. Rep. of Germany ....... 3904872

[51] Int. Cl.⁵ .............................................. B01L 11/00
[52] U.S. Cl. .................................... 422/101; 422/100; 422/102; 436/177; 210/483; 210/484
[58] Field of Search ............... 210/483, 484, 491, 505, 210/503, 508; 422/100, 101, 102; 436/177, 178; 435/294, 295; 604/1; 128/759

[56] References Cited

U.S. PATENT DOCUMENTS

| | | | |
|---|---|---|---|
| 4,554,073 | 11/1985 | Schlüter et al. | 210/450 |
| 4,751,001 | 6/1988 | Saunders | 422/101 |
| 4,765,895 | 8/1988 | Schlüter et al. | 210/491 |
| 4,770,853 | 12/1988 | Bernstein | 422/58 |
| 4,810,394 | 3/1989 | Masuda | 422/101 |
| 4,877,036 | 1/1989 | Saint-Amand | 422/102 |
| 4,973,450 | 11/1990 | Schlüter | 422/101 |
| 4,978,504 | 12/1990 | Nason | 422/58 |

FOREIGN PATENT DOCUMENTS

| | | | |
|---|---|---|---|
| 2155566 | 3/1980 | European Pat. Off. | 422/101 |
| 0235560 | 5/1986 | European Pat. Off. | 210/483 |

Primary Examiner—Robert J. Warden
Assistant Examiner—Laura E. Collins
Attorney, Agent, or Firm—Wallenstein, Wagner & Hattis, Ltd.

[57] ABSTRACT

A method and apparatus for collecting and separating cells, particles or the like from body fluid or the like for microscopic diagnosis is disclosed. Fluid is sucked by capillary action through a fluid-permeable surface (17) which holds back the cell material to be investigated. An apparatus suitable for this purpose comprises a filter container (2) having an upper and a lower opening, the lower opening of which is covered by a fluid-permeable cell carrier element (10), at least one filter segment (11) and a suction insert (12) being arranged in the filter container (2).

9 Claims, 3 Drawing Sheets

METHOD AND APPARATUS FOR COLLECTING AND SEPARATING PARTICLES FROM FLUID FOR MEDICAL DIAGNOSIS

This is a continuation of copending application Ser. No. 07/458,153 filed on Dec. 28, 1989 and now abandoned.

TECHNICAL FIELD OF THE INVENTION

The invention relates to a method for collecting and separating particles or the like from fluid for medical diagnosis, in particular microscopic diagnosis.

BACKGROUND OF THE INVENTION

Known cell separation methods from body fluids operate as a rule by means of filtration, centrifugal force or sedimentation. For this purpose a number of methods and apparatuses have been developed. The majority of these methods is based on the problem of freeing liquids from particles (water processing) and then removing the liquid. In this process the purified fluid or liquid is used again and the particles are discarded. In such methods, particle recovery from the filters used, for example multilayer or depth-type filters, is also not possible.

In laboratory medicine in the investigation of body fluids very different methods are employed each governed by the diagnostic objective or clinical picture. It is known to centrifuge fluid specimens for recovering cells. The sediment is then evaluated via microscopic slide smears. In accordance with the prior art preferably a specific type of centrifugation is employed in which the cell material is deposited from an introduced specimen directly on a microscope slide. The (body) fluid in this process is separated from the particles via the centrifugation process and collected in a fleece paper which is clamped together with the microscope slide in the centrifuge.

Apart from centrifugation methods for cell recovery filtration methods are also employed which are based mainly on membrane filter technology.

If pathological processes, for example neoplasia, are to be detected in body fluids, for example urine the cells relevant to the cytological diagnosis must be isolated in great number and without selection from the overall specimen. The cytologist then makes particularly high demands of the investigation material and the cell recovery method. It is very important here that after recovery of the cells their original state is fully retained, i.e. that the fine morphology of the cells corresponds to the state which they had already during the exfoliation from the tissue into the fluid. In the case of body fluid specimens this is usually material made up in very different ways. Ascites is frequently rich in cells, blood and protein and has a high viscosity. Female urines are richer in cells and more viscous than male urines. Inflammatory processes contaminate the specimens with erythrocytes and leucocytes and also influence the flow rate. Specimens can equally well be mixed with protein, fibrin and blood coagulant. Bacteria destroy cells and lead to permeation of the specimens with detritus.

For cytology of body fluids, and this applies apart from urine to all such fluids as well as to liquor, effusions, ascites and peritoneal cavity lavage, irrespective of the nature of the fluid it must be possible to recover a well preserved cell material.

Known methods used for particle and/or cell recovery still have disadvantages. Thus, it is known that in centrifugation processes a comparatively large amount of cell material can be lost at the walls of the centrifuge glasses, depending on the adhesion behaviour of the cells.

Known membrane filters also have considerable disadvantages; in particular, they cannot be employed for specimens very rich in cells or for highly viscous solutions. Sensitive or predamaged cells are destroyed or modified to a great extent in both methods. Also disadvantageous are filtration methods and apparatuses in which cells are lost. For this falsifies the overall picture of the cytological preparation and there is a danger that small-cell carcinomas are negatively selected.

Known medical diagnostic methods make the following demands of a cell recovery method and the associated apparatuses, although as a rule these demands cannot be met or can be met only incompletely;

Separation of all the cells important for the diagnosis without cell selection or cell loss.

No restriction as regards the particle size. Cells with diameters of 7 $\mu$m and less must be acquired to an equal extent to cell conglomerates with more than 100 $\mu$m diameter.

The viscosity of a solution (of body fluid) must not have any influence on the recovery rate of the cells.

The method must be quick, effective and operate reproduceably as well as being suitable for mass examinations.

To protect the user it must be ensured that any contact with the fluid to be investigated by a person carrying out the test is largely excluded (infection prophylaxis).

After separation of the particles it must be possible to safely dispose of the fluid specimen or to keep it safely in a closed system for other tests.

Finally, it should be possible to fix or conserve particles (cells) separated from the fluid directly after the recovery in a suitable liquid, for example alcohol.

SUMMARY OF INVENTION

The invention is based on the problem of providing a method and an apparatus for collecting and separating particles from a fluid for medical diagnosis which permit reliable medical diagnosis in simple and economic manner.

The method according to the invention for solving this problem is characterized in that the fluid is sucked by means of an absorbent material through a surface to which the particles adhere.

A first apparatus according to the invention for solving this problem is characterized by a first container in which a suction insert (liquid-permeable capillary suction element) sucking up the fluid is arranged and a surface which is arranged in the suction path of the fluid and is permeable for the fluid but not for the particles.

A second apparatus according to the invention for solving the aforementioned problem is characterized by a container which is able to automatically increase its volume to suck in fluid and a surface which is arranged in the suction path of the fluid and is permeable for the fluid but not for the particles.

In a preferred further development of said apparatus the container increases its volume under the action of a spring or due to its intrinsic elasticity.

The method according to the invention and the apparatus for carrying out such a method have a number of advantages. Precisely evaluatable specimens can be obtained without complicated and cost-intensive apparatuses being necessary. The method can be carried out simply and in a short time without requiring specially trained personnel. Furthermore, the method according to the invention and the apparatus is relatively unselective as regards particles (cells) of different size and type, i.e. the recovered particle distribution extensively reflects the actual conditions in the fluid sample to be investigated.

Also, the method according to the invention is relatively gentle, i.e. the cell material to be investigated remains intact to a great extent.

The invention also permits a relatively simple adaptation to various diagnosis methods, for example to the cell recovery from the urogenital tract.

The term "fluid" used here is to be taken broadly. It covers any type of body fluid, i.e. fluid generated by the human or animal body, as well as results of processing of such fluids, for example solutions of body fluids.

The term "particle" in the sense of the invention is to be interpreted broadly and means in particular, but not only, cells.

In a particularly preferred further development of the method according to the invention or an apparatus for carrying out such a method the fluid is sucked by capillary action through the surface to which the particles (in particular cells) adhere.

Instead of capillary action the suction action of the absorbent material can also be generated in another manner, for example by a chemical reaction (hydrophilic material) or by an automatic expansion operation in which a partial vacuum is generated on one side of the surface.

Preferably, the surface is not formed integrally with the absorbent material but as a separate layer. Plastic and acetate fabrics have been found particularly suitable. A particularly reliable measurement is possible with an acetate fabric.

The invention makes it possible with low expenditure to apply cell material to a surface (preparation surface), to fix said material if necessary and thereafter wipe it onto a microscope slide.

As tests have shown separation of all cells important for diagnosis takes place practically without any appreciable loss of cell material. An advantageous further development of the method resides in that before smearing the cell material to be investigated onto a microscope slide substantial parts of the fluid sucked in during the sampling are removed. This not only promotes clean working with correspondingly low danger of infection for personnel but also makes it possible to despatch the cell material for example by post.

An advantageous further development of the method according to the invention resides in that the sucking in of the cell material to be investigated is intensified with the aid of a considerable volume increase of a filter segment. By this particular increasing of the volume of the filter segment the suction action on charging the preparation surface is increased to such an extent that good separation of all cells important for the diagnosis is greatly promoted with rapid and effective mode of operation of the method.

According to a further development of the method the cell material to be investigated and collected on the surface is rendered transportatable in that, possibly after fixing, it is introduced into a sealable container, for example after superfluous fluid has been removed. The cell material to be investigated is then protected from outer influences in a closed transportable container.

It may be desirable to retain in the specimen or also transport further test fluid in addition to the cell material to be investigated and already disposed on the preparation surface. In such a case it is advantageous to additionally add fluid to be investigated within a container receiving the readiness surface, preferably the sealable container.

A preferred further development of the apparatus according to the invention for such an apparatus resides in that the apparatus comprises a filter container which is provided with an upper and lower opening and the lower opening of which is covered by a fluid-permeable but cell-impermeable cell carrier element (particle collection layer), and in the filter container, one behind the other from the bottom to the top, at least one filter segment is arranged after the cell carrier element and thereafter a suction insert. The aforementioned surface is formed on the cell carrier element.

If the lower end of said apparatus provided with the cell carrier element is dipped for example into a container filled with urine a corresponding fluid amount will be sucked through the carrier element and through a filter portion into the suction insert without any kind of additional aids being necessary. The cells, particles or the like cell material to be investigated and separated from the fluid settle on the cell carrier element and the collecting and separating process takes place gently but nevertheless rapidly and quickly.

In particular for despatching separated cell material it is advantageous when the apparatus comprises a sealable container for the lower end of the filter container comprising the cell carrier element.

In particular in the latter embodiment of the apparatus it is advantageous to provide between the sealable and the filter container a fluid seal, preferably in that at least at the lower end of the filter container a fluid seal is disposed. When as usual in transport the sealable container is sealed at its end opposite the cell carrier element and with its other end region or its centre region is in fluid-tight connection with the filter container the result is a housing sealingly enclosing the cell carrier element. This protects the cell material to be investigated from undesirable influences.

An advantageous further development of the apparatus according to the invention resides in that the filter container comprises at its upper end, i.e. that remote from the cell carrier element, a perforated cover or the like upper connection and said perforation is preferably formed as insertion or removal opening for the suction insert. This permits easy removal of said suction insert and thus removal of a quite considerable proportion of the body fluid or the other fluid from which the cell material has been separated.

A particularly advantageous further development of the apparatus resides in that at least a filter segment near the cell carrier consists of a material unfolding sponge-like on contact with fluid, preferably of regenerated compressed cellulose. When such a filter portion increases sponge-like in volume on contact with fluid the suction action of the apparatus is intensified. Regenerated compressed cellulose has been found particularly suitable as material for a filter portion unfolding sponge-like. It also has enough inherent stability to be able to adequately clamp and seal flush with the wall the cell carrier element, consisting of fabric, in particular of dense acetate fabric, in the interior of the filter container. This contributes to the fact that the assembly of the entire apparatus is not only very simple but also does not require for said acetate fabric or the like any undesirable additional holding means which could impair the method for collecting and separating cells.

BRIEF DESCRIPTION OF DRAWINGS

Hereinafter the invention will be described in further detail with reference to the examples of embodiment in conjunction with the drawings. In the drawings, to different scales and schematically.

DETAILED DESCRIPTION OF THE DRAWINGS

Figure 1:
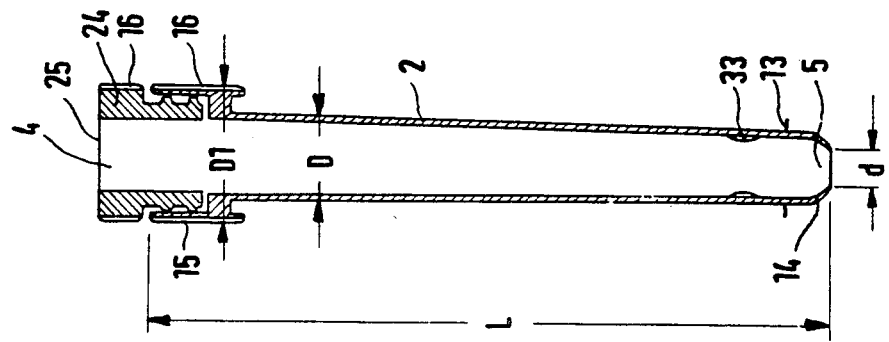
FIG. 1 shows a longitudinal section through an apparatus for collecting cells or the like to the lower end of which a sealable container is fitted.

An apparatus denoted as a whole by 1 comprises a filter container (referred to in the claims as a first container) 2 and a sealable container 3 (FIGS. 1 and 2), referred to in the claims as a second container. Said device or apparatus 1 serves for collecting and separating cells and particles from body fluids or the like for microscopic diagnosis. The filter container 2 has an upper and a lower opening 4 and 5. It is made substantially tubular (FIG. 3). As readily apparent from FIGS. 1, 6 and 7 the lower opening 5 is covered by a cell carrier element 10 (referred to in the claims as a particle collection layer) of dense acetate fabric. The cell carrier element thus extends beyond the bottom of the filter container as shown in FIG. 1 so that the bottom thereof can be immersed in a liquid and then wiped against a slide. In the filter container 2, arranged in series from the bottom to the top, are a filter portion 11 and thereafter a suction insert 12, referred to in the claims as a capillary suction element.

The (empty) filter container 2 is shown in the example of embodiment according to FIG. 3 only somewhat smaller than a possible practical construction. As explained below, it is equipped as hand device with corresponding dimensions and gripping aids. The filter container 2 is preferably made of polyethylene and its total length L is for example 110 mm and its inner diameter D for example 10.5 mm. The filter container 2 has an annular fluid seal 13 which is disposed near the lower end 5. The lower end 5 of the filter container 2 comprises a conical narrowing 14 so that at the lower end or aperture 5 (referred to in the claims as a first aperture disposed at the bottom of the first container) of the filter container 2 a clear opening 5 with a diameter d of for example 6.5 mm results. At the upper end 4 the filter container 2 is provided over the axial length of a grip portion 15 with an enlarged outer diameter D 1. Here radial ribs 16 or a corresponding knurling are provided. Both the diameter enlargement and the ribs 16 are intended to simplify handling.

Figure 7:
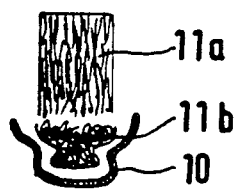
FIG. 7 shows the lower part of the filter container content similar to FIG. 6 also in separated illustration and FIG. 8 shows a further example of embodiment of an apparatus according to the invention.
Figure 6:
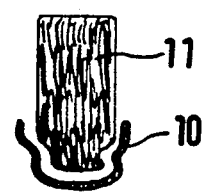
FIG. 6 shows the content of the filter container, i.e. a suction insert, a filter segment and a cell carrier element in separated illustration.

As apparent from FIG. 1 and readily apparent from FIGS. 6 and 7 to a larger scale, in the conical narrowing 14 of the filter container 2 a filter portion 11 (referred to in the claims as an absorbent filter element) is accommodated which for example has a length of about 20 mm. As readily apparent from FIG. 6 the filter portion 11 consists of fibrous material with fibers or highly absorbent material aligned in the longitudinal direction. The parts accommodated in the filter container 2, i.e. the cell carrier element 10 consisting of a portion of dense acetate fabric, the filter portion 11 and the suction insert 12 are fixed in position within the filter container 2.

With the filter container 2 described above it is already possible to carry out a method for collecting and separating cells and particles from fluid for microscopic diagnosis if for example between the collecting and separating of the cells from the fluid and the smearing of the collected cells and particles onto a microscope slide no appreciable periods of time and/or transport paths need be covered. For example, the filter container 2 can be inserted into a test glass with urine and the user waits until the suction insert 12 has absorbed enough fluid. This state is made optically visible in that a cellulose disc 41 (referred to in the claims as a visible indicator) disposed in the upper cap and mounted in intimate contact with the upper end face of the suction insert unfolds upwardly (cf. reference 41 in FIG. 1).

The cellulose disc 41 is impregnated with the filtered body fluid via the suction insert 12 and indicates the final capacity of the system. The swelling operation of the cellulose disc 41 is rendered visible in that the walls of the cap 26 are made transparent. The cellulose can be designated by a yellow or red signal colour.

Instead of the cellulose disc 41 serving as indicator a colour layer consisting of a water-soluble dye may also be inserted. Preferably, the end of the suction insert is impregnated with a dye. The dye, which can be applied moist and bonded by a drying process to the suction insert, is covered towards the top with a disc stamped from fleece paper. When the test fluid has penetrated through the suction insert up to the upper pole the dye dissolves and penetrates the fleece paper disc, the latter colouring. The colouring is visible through the transparent or perforated surface of the cap 26.

This also indicates that an adequate accumulation of cell material is disposed on the surface 17 of the cell carrier element 10. This cell material can be transferred to a microscope slide. If necessary, the collecting operation may be followed by fixing of the cell material with the usual fixing agents, for example alcohol, this being done before the wiping off. This is readily possible if the body fluid is obtained for example from the person to be examined in a clinic and the further investigation method can be carried out on the cell material directly afterwards in the clinic laboratory.

However, the recovery of the cells from the body fluid often takes place a time after or a distance away from the examination. Also, it is often desirable to have the possibility of a second specimen test. Accordingly, the apparatus 1 is so constructed that it comprises if necessary a sealable container 3 for the lower end 5 of the filter container 2 (cf. especially FIGS. 1 to 3). The sealable container 3 and the filter container 2 are adapted to each other in their dimensions and between them the already mentioned fluid seal 13 is provided. Said fluid seal 13 is formed in that an annular sealing lip 13 is provided at least at the lower end of the filter container 2.

Figure 2:
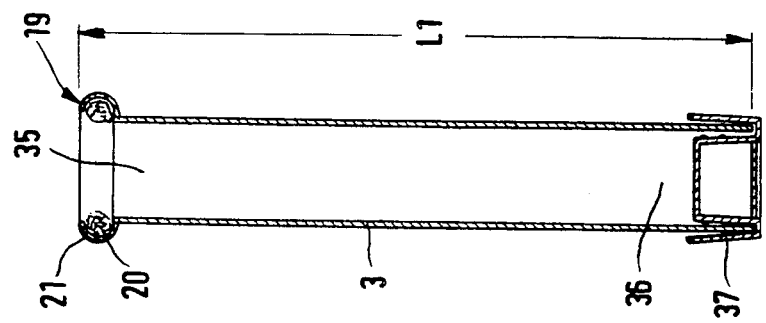
FIG. 2 shows the sealable container according to FIG. 1.
Figure 3:
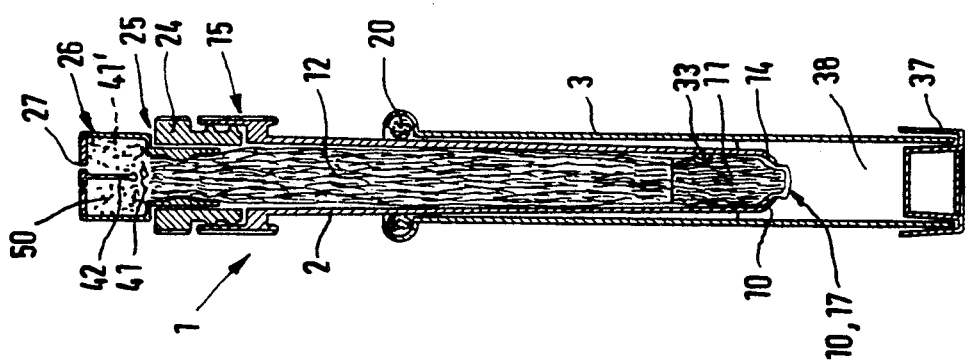
FIG. 3 shows the empty filter container according to FIG. 1.

As readily apparent from FIG. 2 at the upper end 19 of the sealable container 3 around the opening into the container (referred to in the claims as a second aperture) a wiper ring 20 (referred to in the claims as a sealing member) is provided which preferably consists of absorbent material. For this purpose the sealable container 3 comprises at its upper end 19 an outwardly arched holding bead 21 which is of almost U-shaped cross-section and is open towards the interior of the sealable container 3. The wiper ring 20 consisting of absorbent material (referred to in the claims as a fluid absorber disposed in the interior of the second container) is inserted into the resulting annular cavity and when the filter container 2 is inserted into the sealable container 3 (FIG. 1) contacts the outer wall of the filter container 2. This has the advantage that on insertion or withdrawal of the filter container 2 into or out of the sealable container 3 the outer wall of the filter container 2 is automatically cleaned and a user substantially protected from contact with the fluid, thereby considerably reducing the risk of infection. This is also promoted by the grip portion 15 and the associated grip knurling of the grip portion 15.

Contamination of the hands of the user is prevented in particularly advantageous manner in that the filter container 2 and the closure container 3 are formed slightly differently.

Figure 8:
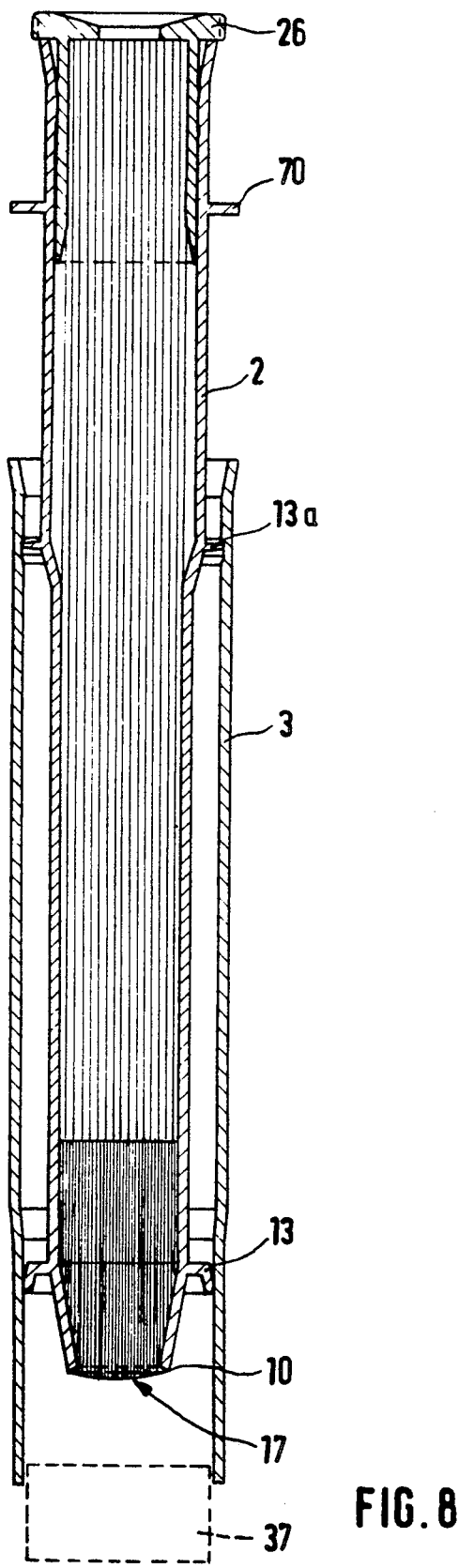

Refer now to FIG. 8 which shows a modified filter container 2. It is readily apparent from FIG. 8 that the filter container 2 comprises near its lower end an encircling sealing lip 13. A further sealing lip 13a is disposed at the upper half of the filter container 2. Also, an encircling stop ring 70 is provided on the container 2 beneath the closure cap zone. The filter container 2 is tapered from the centre towards the lower end. The sealable or closable container 3 is likewise tapered at the lower end so that the sealing lip 13 fits sealingly in said zone in the assembled state of the two parts. The upper opening of the sealable container 3 permits simple insertion of the filter container into the tube. The part of the filter container 2 contaminated in the suction process disappears in the sealable container 3, the contaminated zone being completely sealed between the sealing lips 13 and 13a. The overall system can now be handled and despatched without any risk to the user, providing that the closure caps 26 and 37 also seal the closure container 3.

For transferring cells from the surface 17 to a microscope slide the closure cap 37 is withdrawn from the sealable container 3. The filter container 2 is inserted up to the stop ring 70 into the tube, the cell carrier element 10 moving out of the sealable container 3 to such an extent that the cell material can be transferred without any problem from the surface 17 to the microscope slide (not shown).

It is also apparent from FIG. 1 that the filter container 2 comprises at its upper end 4 a perforated cover 24. The corresponding hole 25 is formed as insertion or withdrawal opening for the suction insert 12. Both the filter container 2 and the cover 24 defining the latter at the top must have an upper opening 4 or the aforementioned hole 25 to enable the desired capillary effect in the suction insert 12 to function for drawing in the fluid. The suction insert 12 of the filter container 2 is rod-shaped and formed as axial abutment for the parts 10 and 11 lying in front thereof. Furthermore, the suction insert 12 is clampingly engaged at its upper end by a cap 26 which itself has an opening towards the outside which is implemented by a hole 27 at the upper end side of the cap 26. A cellulose disc 41 is disposed in said cap 26 above the suction insert 12 and in intimate contact with the latter. Said cellulose disc can expand after absorbing moisture in the cap 26 up to the vent opening.

Figure 5:
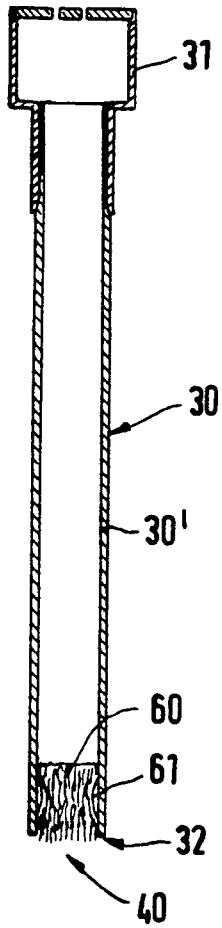
FIG. 5 shows a closure rod to be introduced into the filter container after removal of its suction insert.
Figure 4A:
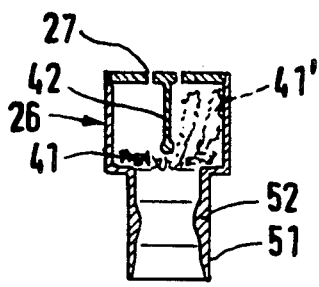
FIG. 4a shows the tap or bushing to be placed onto a suction insert according to FIG. 4.
Figure 4:
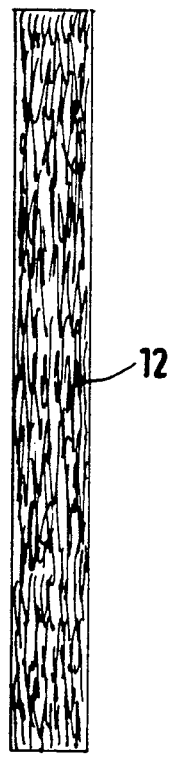
FIG. 4 shows the filter container insert to be introduced into the empty filter container according to FIG. 3 but without a cell carrier element.

The device 1 as readily apparent in particular from FIG. 1 has associated therewith a closure rod 30 (cf. FIG. 5). Said rod is adapted in its dimensions to the withdrawal opening 25 for the suction insert 12 and the cap 26 disposed there. After withdrawal of the suction insert 12 from the filter container 2 the closure rod 30 can be inserted into the withdrawal opening 25. The closure rod 30 is equipped with a cap 31 so that it can be secured to the filter container. This is effected in the example of embodiment in that the cap 31 is adapted on at least one portion to the hole 25 of the cover 24 so that the closure rod can be clampingly located there. Furthermore, the closure rod 30 is dimensioned with its inner end 32 so that said inner end forms an abutment for the filter portion 11 in the filter container 2 (cf. FIGS. 4 and 5). With the closure rod 30 formed in this manner and axially fixed in the filter container 2 an axial fixing of the parts remaining in the filter 2 after removal of the suction insert 12 is achieved, in particular the parts 10 and 11 and the part 11b still to be explained.

The filter segment (porous expandable element) 11b (referred to in the claims as a porous expandable element) is made from a material unfolding sponge-like on contact with fluid. Tests have shown that regenerated compressed cellulose is particularly suitable as such a material. If for example a partial filter segment 11b indicated in FIG. 7 in dot-dash line consists of regenerated compressed cellulose and comes into contact with (body) fluid it tends to expand to a considerable extent, for example up to the front face of the absorbent filter element 11a (FIG. 7). By this axial expansion movement the suction effect is intensified. The expansion possibility of the filter segment 11 expanding axially is limited on the one hand by the lower conical end of the filter container 2 in conjunction with the cell carrier element 10 disposed there and on the other hand upwardly by abutment of the parts 11a and 12.

The filter segment 11 and possibly also its sub-segment 11b consisting of regenerated compressed cellulose is made microporous and has substantially pores of the pore size of at the most 5 $\mu$m. Said maximum pore size also contributes to as little as possible cell material being able to reach the filter container 2 or its suction insert 12 when the fluid is sucked up. The suction insert 12 preferably consists of compressed polyester and cellulose fibres arranged in the longitudinal direction. Said suction insert 12 has practically no filter action but a pronounced suction action.

As readily apparent from FIGS. 1 and 2 the sealable container 3 is also tubular and provided with an upper and lower opening 35 and 36. With the upper opening 35 the sealable container 3 can be placed on the lower end 5 of the filter container which then forms the closure of the upper opening 35. At the lower end 36 of the closure container 3 a removable closure cap 37 is provided. This closure cap 37 makes it possible inter alia to expose the surface 17 of the filter container 2 even when said filter container 2 is already disposed within the sealable container 3. For example, fixing agent can subsequently be introduced into the sealable container 3 and thus also onto the surface 17 and thereafter the sealable container 3 sealed again by means of the closure cap 37. Also, additional body fluid to be investigated can be introduced in the cavity 38 forming between the closure cap 37 and the lower end 5 of the filter container 2 in the closure container 3. The size of the cavity is variable with certain limits because the filter container 2 is displaceably telescopically mounted in the sealable container. The sealable container 3 is likewise preferably made from polyethylene and is tubular and has for example a length L 1 of 110 mm. Beneath the holding bead 21 already mentioned and disposed at the upper end 35 of the sealable container 3 there is a wiper ring 20 which preferably consists of foam material. The holding bead 21 can easily be made by widening the tubular sealable container body and beading over its upper end inwardly (FIG. 2).

The part 11b of the filter segment 11 consisting of regenerated compressed cellulose develops as already mentioned a very pronounced swelling behaviour when it comes together with water, body fluid or the like and thus also a very pronounced ability to absorb fluid. As an example for the material used in the compressed state a density of 0.58 g/ccm is measured and in the dry state after swelling a density of 0.06 g/ccm. When the compressed cellulose, indicated as part 11b of the filter segment 11 in FIG. 7, comes into contact with water or body fluid a lattice structure develops in the compact. The porousness and the size thereof is governed by the expansion possibility of the part 11b of the filter segment 11. In the example of embodiment according to FIGS. 1 and 7 the expansion possibility of the part 11b of the filter segment 11 is limited in that the compressed cellulose itself impinges at the top against the filter segment 11a which is held by an annular bead 33 (FIG. 1).

In accordance with the method according to the invention the apparatus 1 is operated as follows:

A filter container 2 which is first disposed with its lower end 5 in a sealable container 3 and together with the latter in a closed package has the cell carrier element 10, the filter segment 11, the suction insert 12 and the cover 24. In the assembled state shown in FIG. 1 of filter container 2 and sealable container 3 the latter also protects in particular the surface 17 and the lower portion of the filter container 2 which is subsequently dipped into the body fluid or the like. Thereafter the filter container 2 is removed from the sealable container 3 and said filter container 2 dipped with its lower end 5 into a container in which body fluid (e.g. urine) is disposed from which cells, particles or the like cell material are to be collected and separated. The fluids to be examined may also be of other origin, for example from an abdominal cavity lavage. In the filter container 2 by capillary action the fluid is then sucked through the surface 17 and the cells and particles to be investigated remain adhering on the surface 17 which is formed by the cell carrier element 10 of acetate fabric. The one-part of multipart filter segment 11 or 11a and 11b as well as the suction insert 12 suck the fluid through the acetate fabric. If for example a sub-segment 11b of regenerated compressed cellulose is disposed in the filter container 2 said portion begins to unfold in the limited space available to it. The space available and the material are so configured that only pores with a size usually less than 5 μm form. The fluid rises very rapidly in the filter container 2, this being further promoted by the suction action of the initially compressed cellulose part 11b. Finally, said fluid, at least the very greater part thereof, is absorbed by the suction insert 12 and the cellulose disc disposed thereabove and stored therein. This also results, as particularly advantageous effect, in the cell material to be investigated and rising with the fluid collecting quantitatively and gently at the outer layer of the cell carrier element 10, i.e. on the surface 17. "Quantitatively" is to be taken here as meaning that comparatively large amounts of cell material collect on the surface 17. Thereafter, cell material to be investigated can be transferred therefrom by impression to a microscope slide or also by rinsing off into a fluid. The surface 17 can therefore be considered a preparation surface.

Before wiping of the cell material to be investigated the suction insert 12 is removed together with the cap 26. Instead of said parts 12, 26 the closure rod 30 (FIG. 5) is inserted into the filter container 2. Said closure rod 30 effects an axial locating of the filter portion 11 and thus also indirectly represents an abutment for the cell carrier element 10. Tests have shown that a few minutes after the immersion of the filter container 2 into the fluid to be investigated about 6 ml sample fluid have risen through the filter segment 11 into the suction insert 12. The corresponding amount of cell material has then deposited on the surface 17 and can then be transferred directly to a microscope slide, coloured and microscopically examined.

If the cell material to be examined cannot be transferred to a microscope slide and correspondingly treated directly after the operation described above, but must first be sent to a cytology laboratory (diagnosis laboratory) for investigation, the following procedure can be adopted:

The filter container 2 is inserted into the sealable container 3. When this is done fluid which has contaminated the outer wall of the filter container 2 is wiped off at the wiper ring 20 of the sealable container 3. This avoids soiling of the hands of the operator. The suction insert 12 is now withdrawn from the filter container and discarded. If the cell material adhering to the preparation surface 17 is to be preserved for despatch the closure cap 37 of the sealable container 3 can be removed and a suitable fixing solution introduced into the sealable container 3, possibly also the surface 17 specifically sprayed with a suitable fixing solution. The cell material to be investigated is thus wetted by the fixing medium and a cell-destroying lysis prevented from occurring during the despatch of the apparatus 1. Furthermore, a closure rod 30 is introduced into the filter container. Such a closure rod is closed at its inner end face 40 and consists preferably of polystyrene. The closure rod 30 prevents the filter segment 11 or a subsegment 11a or 11b from moving; the closure rod 30 also prevents fluid or other undesired constituents emerging from the filter segment 11 or the like 11a, 11b or being able to enter via said filter segment 11 or 11a and 11b. The apparatus 1 can then easily be despatched.

If the task of cell recovery makes it necessary the cavity 38 of the sealable container 3 disposed in front of the surface 17 can be enlarged by a correspondingly retracted position of the filter container 2, for example up to a capacity of about 10 ml. Said cavity 38 can then for example be filled with an additional specimen fluid of the same patient. The apparatus 1 is then set up with the filter segment 11 pointing upwardly and the following procedure can be adopted: The closure rod 30 is replaced by a new suction insert 12 and the aforementioned additionally added specimen fluid is sucked from above downwardly by the filter and the cells disposed in said additional specimen fluid can be deposited on the surface 17 for example additionally to those already present. In this manner the amount of cell material made available for the test can be increased. Thereafter, the transfer of the cell material to be microscope slide is effected in the usual manner. In FIG. 5 at the lower end of the closure rod 30 an insert 60 of limited absorbent capability can be seen. The closure rod 30 is made substantially tubular, the tube portion being denoted by 30'. Near its inner end the closure rod 30 has an annular radially inwardly projecting holding bead 61 which fixes the insert 60 in the axial direction. Accordingly, the free end face 40 of the absorbent insert 50 formed as abutment can again form an abutment for the parts 11, 11a and 11b (cf. FIGS. 5, 1 and 6 and 7).

It may be desirable to remove some fluid from the filter segment 11 or the corresponding filter segment parts 11a and 11b after the insertion of the closure rod 30 into the filter container 2. In this case the construction of the closure rod 30 with the insert 60 of limited absorbent capability is particularly advantageous.

In another case in which the aforementioned suction operations are not necessary or not desirable the closure tube 30 can have a non-absorbent end plate as termination.

In FIG. 6 the filter container 2 itself is omitted and the content thereof shown in separated representation. Seen from the top to the bottom in FIG. 6 the suction insert 12, a filter segment 11 and, spaced therefrom, a cell carrier element 10 of dense acetate fabric are visible.

In FIG. 7 the lower part of the content of the filter container 2 is shown in somewhat modified configuration, likewise in separated representation. Apparent therein are a shortened filter segment 11a and the filter segment 11b which is made from a material which can unfold sponge-like on contact with fluid, such as regenerated compressed cellulose. In the construction according to FIG. 7 at the inner end of the filter container 2 the space conditions can be so chosen that the filter segment 11b can also increase in volume adequately to a predetermined extent. This can for example be achieved by a corresponding free space or by a certain compressibility in the filter segment 11a.

The fluid absorption capacity of the content of the filter container and possibly of the disc 41 of the sleeve 26 are adapted in a preferred embodiment of the apparatus 1 to the fluid to be investigated so that when the suction capacity of the parts in the filter container 2 and possibly of the disc 41 in the sleeve 26 is exhausted enough cell material to be investigated for the test has collected on the cell carrier element 10 or its surface 17. The aforementioned absorbent capacity of the parts disposed in the filter container 2 is governed in particular by the suction insert 12 therein, the filter segment 11 and the sub-segments 11a and 11b of the filter segment and possibly by the absorbent capacity of the cellulose disc 41 disposed in the cap or sleeve 26.

All the features described above and/or set forth in the claims can be essential to the invention individually or in any combination with each other.

I claim:

1. A medical diagnostic apparatus for collecting and separating particles from a liquid comprising:

a first container having a first aperture disposed in one end of said first container serving as a bottom thereof for vertical immersion into a liquid to a given depth;

at least one liquid-permeable capillary suction element within said first container for drawing said liquid into said element by capillary action when in contact with said liquid; and a particle collection layer separate from said capillary suction element and permeable to fluids but not to particles and disposed to cover said first aperture so that when said first aperture is dipped into said liquid said capillary suction element draws said liquid upwardly through said layer and into contact with lower portions of said capillary suction element to deposit said particles on an outside bottom surface of said layer, said first container having a portion thereof above said first aperture configured as an elongated shape to be graspable by a user and to be moved about so that the bottom thereof can be immersed in a liquid body and then wiped against a slide, at least portions of said article collection layer extending beyond the bottom of said first container so that said layer can be wiped onto a slide to allow particles collected on said layer to be removed and examined.

2. The apparatus of claim 1 including a porous expandable element provided in unexpanded form within said first container and having the property of undergoing significant expansion when wetted by liquids to expand the porosity volume therein so as to augment the capillary flow induced by said capillary suction element.

3. The apparatus of claim 2 wherein said expandable element is disposed below said capillary suction element and in confronting relationship with said particle collection layer so that upon expansion said expandable element pressingly engages the periphery of said layer to force it against the first container.

4. The apparatus of claim 2 wherein said layer is disposed within said first container against the walls thereof surrounding said first aperture, said expandable element being disposed in confronting relationship with said layer so that the expansion of said expandable element securingly compresses said layer against an interior surface of said first container.

5. The apparatus of claim 3 including an absorbent filter element having a plurality of fibers therein aligned parallel to each other and to the direction of flow of said liquid, said absorbent filter element being disposed between said capillary suction element and said expandable element.

6. The apparatus of claim 1 including a visible indicator in an upper portion of said first container for providing a visible indication that said capillary suction element has been filled by said liquid.

7. The apparatus of claim 6 further comprising a second container having a second aperture in a portion of the walls thereof for insertingly accepting at least a portion of said first container containing said first aperture; and a sealing member associated with said second aperture for providing a sealed volume between the walls of said first and second containers.

8. The apparatus of claim 7 including a fluid absorber disposed in the interior of said second container.

9. The apparatus of claim 1 wherein said layer is configured with an outer portion disposed to abut an interior surface of said first container and a central portion configured to pass through said aperture and beyond said bottom of said first container.

* * * * *